United States Patent [19]

Pall et al.

[11] 4,431,545

[45] Feb. 14, 1984

[54] MICROPOROUS FILTER SYSTEM AND PROCESS

[75] Inventors: David B. Pall, Roslyn Estates; Abraham Krasnoff, Glen Cove, both of N.Y.

[73] Assignee: Pall Corporation, Glen Cove, N.Y.

[21] Appl. No.: 376,259

[22] Filed: May 7, 1982

[51] Int. Cl.³ .................... B01D 13/00; B01D 31/00
[52] U.S. Cl. ................................. 210/641; 210/650; 210/500.2
[58] Field of Search ............... 210/641, 650, 651, 654, 210/685, 686, 806, 321.1, 321.5, 433.2, 493.1, 493.5, 500.2, 506, 638; 521/27

[56] References Cited

U.S. PATENT DOCUMENTS

| | | | |
|---|---|---|---|
| 3,132,094 | 5/1964 | McKelvey et al. | 521/27 |
| 4,253,900 | 3/1981 | Dege et al. | 521/27 |
| 4,288,462 | 10/1981 | Hou et al. | 426/423 |
| 4,340,479 | 7/1982 | Pall | 210/500.2 |
| 4,350,594 | 9/1982 | Kawai et al. | 210/641 |

*Primary Examiner*—Ivars C. Cintins

*Attorney, Agent, or Firm*—Leydig, Voit, Osann, Mayer and Holt, Ltd.

[57] ABSTRACT

A microporous filter system comprises two types of hydrophilic, microporous filter media operating in series. The two filter media have opposite zeta potentials with the upstream or first filter medium preferably having the positive zeta potential and the downstream or second filter having the negative zeta potential. The first filter medium typically has an absolute pore rating of from about 0.1 to about 1.0 micrometer and the second or downstream filter medium typically has an absolute pore rating of from about 0.02 to about 0.1 micrometer. The downstream or second filter has a finer absolute pore rating than the upstream or first filter. Fluids contaminated with ultrafine particles can be purified with an essentially absolute efficiency to remove 99.99 percent or more of the particulate matter in the contaminated fluid. The filter system finds particular use in the preparation of ultrapure effluent water of near theoretical resistivity and in the removal of bacteria and endotoxins to form sterile fluids.

19 Claims, No Drawings

MICROPOROUS FILTER SYSTEM AND PROCESS

TECHNICAL FIELD

The present invention relates to a microporous filter system. More particularly, the invention relates to a novel microporous filter system with enhanced filtration efficiencies for the removal of ultrafine particulates and hence effective in the ultrafiltration range.

BACKGROUND ART

To appreciate the significance of the subject invention, it is necessary that certain terms used herein be defined. In this regard, the terms "ultrafiltration" and "ultrafilter" are commonly used, and will be used herein, to describe a filtration process and a filter respectively having the ability to remove particles as fine as about 0.001 micrometers up to about 10 micrometers (microns), a range of particle sizes commonly referred to as "ultrafine". Ultrafiltration media with very fine pore sizes are recognized as useful for filtering ultrafine particles from various liquid media. Unfortunately, ultrafilters in general have efficiencies below 100 percent in the range of below 0.1 micrometers.

The term "efficiency", as used herein, means the ability of a filter medium to remove particulate contaminant of a given type, that is, it is the percent of that particular type particulate contaminant which is unable to pass through the filter. For example, to refer to a filter medium with an efficiency of 100 percent for a given type particle means that the effluent from that filter contains none of that particular species of particulate contaminant, whether that species is characterized by size alone, the electrocharge on the particle, another property of the particle, or a combination of such characteristics. As used herein the term "essentially absolute efficiency" means the ability to remove a particular particulate contaminant at the 99.99 percent level or better. Correspondingly, the term "substantially free" of a particular contaminant means that the level of the particular contaminant in the effluent from the filter system has been reduced by 99.99 percent of its influent concentration and, in some cases, to substantially lower levels.

The function of a filter is the removal of suspended particulate material and the passage of the clarified fluid medium (filtrate or effluent). A filter can achieve fluid clarification by different mechanisms. Particulate material can be removed through mechanical sieving, wherein all particles larger than the pores of the filter are removed from the fluid. With this mechanism, filtration efficiency is controlled by the relative size of the particulate contaminant and the physical pore size of the filter. The efficient removal of very small particles, e.g., less than 0.1 micrometer in diameter, requires ultrafilters with very small pore sizes. Such fine pore filters tend to have the undesirable characteristics of high pressure drop across the filter, reduced dirt capacity and shortened filter life, resulting in an inefficient and uneconomical means for providing high level purification of contaminated fluids. These problems are exacerbated by the almost invariable tendency for the skinned membranes, typically used as ultrafilters, to have pin holes providing the highly undersirable result (for some applications) of allowing larger size particles to penetrate the filter, thereby contaminating the downstream filtrate with, e.g., bacteria, rendering such ultrafilters incapable of being used for providing a sterile filtrate. Such membranes are poorly suited, then, wherever essentially absolute efficiency for the removal of ultrafine particulate material, i.e., wherever complete removal of incident bacteria is required.

A filter may also remove suspended particulate material by adsorption onto the filter surfaces, that is, the surfaces of the pores in the filter. Removal of particulate material by this mechanism is controlled by the surface characteristics of (1) the suspended particulate matter, and (2) the filter. Most suspended solids which are commonly subjected to removal by filtration are negatively charged in aqueous systems. This feature has long been recognized in water treatment processes where cationic flocculating agents, oppositely charged to the suspended matter, are employed to improve settling efficiencies during water clarification.

Colloid stability theory can be used to predict the interactions of electrostatically charged particles and filter surfaces. If the charges of the suspended particles and the filter surfaces are of like sign and with zeta potentials of greater than about 20 mV, mutual repulsive forces will be sufficiently strong to prevent capture by adsorption. If the zeta potentials of the suspended particles and the filter surfaces are small or, more desirably, of opposite sign, the particles will tend to adhere to the filter surfaces with high capture efficiencies. Most particles in the suspensions encountered in industrial practice have a negative zeta potential. Thus, microporous filters characterized by positive zeta potentials are capable, in a large number of industrial applications, of removing particles much smaller than the pore diameters of the filter through the mechanism of electrostatic capture. As a result, the high pressure drops, reduced dirt capacity and shortened filter life encountered with a filter operating strictly as a mechanical sieve can, to a large extent, be avoided.

The drawback of a filter operating as an adsorption filter by virtue of interaction between the particulates being filtered and the surfaces of the filter medium is that such a filter with a given zeta potential (positive or negative) will not capture similarly charged particulates smaller than the physical pore size of the filter, due to the mutually repulsive forces of the particles and the filter surfaces. Thus, for example, fine asbestos particles which carry a positive charge will not be removed from fluid media passed through a filter medium having a positive zeta potential except by a sieving mechanism as discussed above.

Similarly, with particulates of little or no charge, e.g., some bacteria and endotoxins as well as some other particulates, the only assured way of removing these materials by a filtration process is by a sieve mechanism. The conundrum has been that a filter with physical pore sizes fine enough to capture very fine particulates by a sieve mechanism quickly develops a high pressure drop as particulate matter clogs these fine pores, the limited capacity of the filter is quickly reached and the filter life is shortened to the point that economic ultilization of such filters is restricted.

The present invention is directed to novel filter systems capable of greatly enhanced filtration efficiency over a broad pH range and with a wide variety of particulate contaminants, including ultrafine particulates, particularly very fine negatively charged particles, very fine positively charged particles, and substantially neutrally or uncharged particles. The filter systems of this invention have extended lives relative to conventional fine pored ultrafilters, such as skinned membranes, because of the unique combination of filter media which serves to protect the very fine pored, downstream, last chance or final filter.

Filter systems of the present invention are also capable of delivering high purity effluent water rapidly after the onset of filtration, the purity level being such that the resistivity of the effluent water rapidly reaches the theoretical resistivity of water, i.e., greater than 14 megaohms/cm. This ability makes filter systems of this invention particularly desirable for the filtration of aqueous fluids employed in microelectronics manufacture where ever increasing packing densities in microcircuits are forcing the manufacturers to seek filtration systems with the ability to remove very fine contaminants from their processing liquids. Further, filter systems of this invention have the capability of removing very fine contaminants from process liquids, such as the water used by electronics manufacturers to make microcircuits, without the large capital investments presently typical for installation of conventional ultrafiltration systems.

DISCLOSURE OF INVENTION

This invention is directed to microporous filter media for the removal of particulates from fluid media, particularly ultrafine particles, at an essentially absolute efficiency, i.e., 99.99 percent or higher level, for both negatively charged and positively charged particulate contaminants as well as neutral or uncharged particulate contaminants, e.g., some bacteria, endotoxins and particulates.

The process of the subject invention provides for the filtration of a contaminated fluid comprising submicronic particulate matter which may include any or all of the above-described contaminants, the process comprising:

(a) passing the fluid through a first filter medium comprised of a hydrophilic, microporous member having a positive zeta potential to remove electronegatively charged particulate matter from said fluid; and (b) then passing the fluid (substantially free of electronegatively charged particulate matter) through a second filter medium comprised of a hydrophilic, microporous member having a negative zeta potential and an absolute pore rating finer than that of the first filter medium to form a filtrate substantially free of (1) both electronegatively and electropositively charged particulate matter and (2) particulate matter greater in size than the absolute pore rating of the second filter medium.

As discussed in more detail hereinafter, the order of the two filter media described above, that is the positive and negative zeta potential filter media, can be reversed. However, whichever filter medium first sees or contacts the contaminated fluid, the second filter medium in series should have the finer absolute pore rating.

The first filter medium is preferably comprised of a surface modified, hydrophilic, microporous polyamide membrane having positive zeta potential and an absolute pore rating of from about 0.05 to about 1.0, preferably from about 0.1 to about 0.5 micrometer.

The second filter medium preferably is comprised of a hydrophilic, microporous polyamide membrane having a negative zeta potential and an absolute pore rating of from about 0.01 to about 0.1, preferably from about 0.02 to about 0.06 micrometer.

The combination of these two preferred filter media, either in the form of a composite filter sheet or as separate filter elements operating in series, provides an ultrafiltration system for the removal of positively and negatively charged particles down to essentially molecular dimensions at an essentially absolute efficiency together with substantially complete removal, i.e., at the 99.99 percent level or higher, of ultrafine particulate matter of substantially neutral or uncharge nature down to a size as small as about 0.01 micrometer.

The two stage ultrafilter system of this invention finds particular use in the preparation of effluent water of near theoretical resistivity, i.e., greater than 14 megaohm/cm, after very short onstream times.

BEST MODE FOR CARRYING OUT THE INVENTION

As described above, the subject invention is directed to a filter system and a process for using it. The filter system is comprised of two microporous filter media with zeta potentials of opposite sign operating in series. Preferably, the upstream filter medium, which first contacts or sees the contaminated fluid containing submicronic particulate suspended or dissolved material, has a positive zeta potential since the vast majority of contaminated fluids encountered in industrial applications contain a larger proportion of negatively charged particulate matter than positively charged. However, in either this preferred embodiment or the alternative, where the negative zeta potential filter medium is upstream of the filter medium having a positive zeta potential, the downstream or second filter medium should have an absolute pore rating smaller than that of the upstream or first filter medium. In this manner, the finer pored downstream or second filter medium has a longer filter life since it does not become clogged with the relatively large particles taken out by the coarser upstream or first filter medium.

FILTER MEDIUM WITH A POSITIVE ZETA POTENTIAL

To perform satisfactorily as the filter medium with a positive zeta potential in the upstream position, i.e., as the first filter medium, the particular medium chosen should have the following characteristics:

(1) a positive zeta potential under the conditions encountered during the filtering operation;

(2) a microporous structure, typically with an absolute pore rating in the range of from about 0.05 to about 5.0 micrometer; and (3) be hydrophilic, i.e., readily wetted by water, which is visually observable by the rapid spreading of a drop of water placed in contact with the filter medium.

When a filter medium with a positive zeta potential is used as the downstream filter medium, it should have the same chacteristics described in (1) to (3) above except that the absolute pore rating must be finer than the upstream or first filter. Typically, then, the absolute pore rating will be reduced to be in the range of from about 0.01 to about 0.1 micrometer, preferably from about 0.02 to about 0.06 micrometer.

The preferred filter media having a positive zeta potential, when used as either the first "coarser" filter medium or as the "finer" second filter medium are the surface modified, hydrophilic, microporous, polyamide membranes of the type disclosed in detail in copending applications, U.S. Ser. No. 312,722, filed Oct. 19, 1981, entitled "Charge Modified Polyamide Membrane"

(contacting technique) and U.S. Ser. No. 346,119, filed Feb. 5, 1982, entitled "Surface Modified Polyamide Membrane" (cocasting technique). The disclosures of these two copending applications are incorporated herein by reference. Basically, the surface modified polyamide membranes described in these two copending applications which are useful in the filter system of this invention have the following characteristics:

1. a positive zeta potential over the pH range of from about 3 to about 10;
2. an absolute pore rating of from about 0.01 micrometers; and
3. an essentially absolute efficiency for removal of negatively charged particulate matter down to molecular dimensions.

These hydrophilic, surface (charge) modified, microporous polyamide membranes can be prepared using the methods described in the two copending applications identified immediately above. These processes and the resulting products are described below:

COCASTING TECHNIQUE OF U.S. SER. NO. 346,119

Surface (charge) modified, hydrophilic, microporous, polyamide membranes are prepared by the steps of (1) preparing a casting solution comprised of (A) a casting resin system comprised of (a) an alcohol-insoluble polyamide resin having a ratio $CH_2$:NHCO of methylene $CH_2$ to amide NHCO groups within the range of from about 5:1 to about 7:1, nylon 66 being a preferred polyamide resin, and (b) a membrane surface modifying polymer; and (B) a solvent system in which the casting resin system is soluble, such as a mixture of formic acid and water; (2) inducing nucleation of the casting solution by controlled addition of a nonsolvent (such as water) for the casting resin system under controlled conditions of concentration, temperature, addition rate and degree of agitation to obtain a visible precipitate of casting resin system particles which may or may not thereafter partially or completely redissolve, thereby forming a casting composition; (3) preferably filtering the casting composition to remove visible precipitated particles; (4) spreading the casting composition on a substrate to form a thin film thereof on the substrate; (5) contacting and diluting the film of casting composition with a liquid nonsolvent system for the casting resin system comprised of a mixture of solvent (such as formic acid) and nonsolvent liquid (such as water) and containing a substantial proportion of the solvent liquid but less than the proportion in the casting composition, thereby precipitating the casting resin system from the casting composition in the form of a thin, skinless, hydrophilic, surface modified, microporous membrane; (6) washing the membrane; and (7) drying the membrane.

The resulting surface modified, microporous, alcohol-insoluble polyamide membranes are hydrophilic, i.e., they are readily wetted by water. They have absolute pore ratings of from about 0.01 up to about 10 micrometers or more and modified zeta potentials, i.e., strongly positive zeta potentials, over the pH range of from 3 to 10. The membranes of this type, when used in this invention as the first filter medium in the upstream position, will typically have absolute pore ratings of from about 0.05 to about 1.0 micrometer, preferably from about 0.05 to about 0.2 micrometer. When membranes of this type are used as the second or final filter medium in the downstream position, they will typically have absolute pore ratings of from about 0.01 to about 0.1 micrometer, preferably from about 0.02 to about 0.06 micrometer.

The membrane surface modifying polymers or resins useful in preparing these membranes are the cationic, water-soluble, quaternary ammonium, thermosetting polymers. Preferred polymers within this class are the epoxy-functional polyamido/polyamino-epichlorohydrin resins. The epoxy-functional polyamine-epichlorohydrin resins are particularly preferred.

COATING TECHNIQUE OF U.S. SER. NO. 312,722

Charge (surface) modified, resin coated, hydrophilic, microporous polyamide filter membranes may be prepared by contacting a skinless, hydrophilic, microporous polyamide membrane (such as those disclosed in copending U.S. Ser. No. 198,570, filed Oct. 20, 1980 as discussed hereinafter) with a solution of a water-soluble, non-colloidal, cationic, thermosetting resin, removing any excess solution from the membrane, drying the membrane and curing the thermosetting resin to form a cured coat of the resin on the micropores of the membrane. The resulting coated microporous membranes have a positive zeta potential in alkaline media and preferably over a pH range of from about 3 to about 10, and absolute pore ratings as fine as about 0.01 up to about 10 micrometers. The membranes of this type, when used as the first filter medium in the upstream position, will typically have absolute pore ratings of from about 0.05 to about 1.0 micrometer, preferably from about 0.05 to about 0.2 micrometer. When used as the second or final filter medium in the downstream position, the membranes of this type will typically have absolute pore ratings of from about 0.01 to about 0.1, preferably from about 0.02 to about 0.06 micrometer.

A preferred product of this type for use in this invention is a hydrophilic, microporous, nylon 66 membrane which has been coated with a polyamine-epichlorohydrin resin. A preferred process for preparing the filter membranes of this invention is to remove the excess solution referred to above by vigorous water wash. It is also desirable with some resins that an ion exchange be carried out to render the membrane less susceptible to undesirable shifts in the pH of filtrate water flowing through the treated membranes. Additionally, in certain applications where an ultrapure water is required, such as electronics manufacture, the filter membrane may be subjected to a water treatment after the resin has been cured. This treatment comprises flowing very pure water through the filter membrane until the filtrate downstream of the filter membrane has the desired level of purity.

Other materials may be used as the filter medium with a positive zeta potential provided they meet the criterion set out above, namely a positive zeta potential under the conditions encountered in the filtering process, a microporous structure with appropriate absolute pore ratings, typically in the range of from about 0.05 to about 1.0 micrometer when used as the upstream or first filter and from about 0.01 to about 0.1 micrometer in the downstream or second filter, and hydrophilicity. A conventional ultrafilter which is typically a skinned membrane is undesirable for this purpose for the reasons described above.

Other filter media with a positive zeta potential satisfactory for use as the first filter medium include hydrophilic, polymeric, microfibrous filter sheets. These filter sheets and their method of preparation are the invention of David B. Pall, one of the inventors in this case, and two of his associates. A patent application is being prepared covering this subject matter, U.S. Ser. No. 397,762 filed July 13, 1982 entitled "Polymeric Microfibrous Filter Sheet And Method Of Preparation", the disclosure of which is incorporated herein by reference. These types of filter media can be prepared as follows:

METHOD OF PREPARATION OF HYDROPHILIC, MICROFIBROUS, POLYMERIC FILTER SHEETS

The general method of preparing hydrophilic, microfibrous, polymeric filter sheets comprises four steps:

(1) applying a first solution or dispersion of a precipitating agent to a hydrophobic web comprised of polymeric microfibers to at least partially wet the web with this first solution;

(2) applying a second solution of a water-soluble, non-colloidal, cationic, thermosetting binder resin or polymer to the wetted web of step (1) above to form a web wetted with a mixture of the first solution or dispersion and the second solution;

(3) working the wetted web of step (2) above to mix the first solution or dispersion, thereby facilitating the precipitation of the binder resin or polymer and the distribution in a uniform manner of the precipitated binder resin or polymer as a coating on the surfaces of the microfibers making up the worked web; and (4) drying the coated web of step (3) above and curing the precipitated binder resin or polymer coating to provide a hydrophilic, microfibrous, polymeric filter sheet with a positive zeta potential and which is further characterized by the surfaces of the microfibers therein being coated with a cured, precipitated, thermoset, cationic binder resin or polymer.

Variations in the four basic process steps outlined above, as well as certain additional processing steps, may be utilized in practicing the process of this invention. For example, steps (1) and (2) above can be reversed, albeit the preferred order of application is as set out above. Additionally, it may be desirable in certain instances to use prewetting solutions containing a wetting agent such as a surfactant, or a lower alcohol in aqueous solution to prewet the hydrophobic webs, followed by water washing to remove at least the major portion of the wetting agent from the web, preferably as completely as possible, while maintaining the web in a water wetted form, and then applying the first and second treating solutions as described above or in reverse order. (Herein, the terms "solution" or "treating solution" are sometimes used in describing processing under steps (1) and (2) above.) It should be understood that when the precipitating agent containing composition is being referred to it may be present as either a solution or a dispersion.

Additionally, it may be desirable, with some carboxylate precipitating agents, to convert some of the carboxylic acid groups therein to their salt form by neutralization with inorganic bases, e.g., sodium hydroxide, or organic bases, e.g., diethanolamine or triethanol amine. This treatment improves the solubility of the precipitating agent and, in some instances, improves the wetting characteristics of the solution or dispersion of the precipitating agent in the treatment of the hydrophobic web, thereby permitting the deletion, in some cases, of the prewetting steps referred to above. When the binder resin or polymer is used as the first solution, i.e., when it is applied to the web first in step (1) above, similar materials may be desirable for the same reasons, particularly for improving the wetting characteristics of the binder resin or polymer solution. Indeed, for some webs with a lesser degree of hydrophobicity, the prewetting step can be avoided by the use of diethanolamine or a similar material as a component of the first solution applied.

Preferably, the hydrophobic web is fully wetted, i.e., saturated, in step (1) above, i.e., with the first solution added, whether that be a solution of the precipitating agent or the solution of the binder resin or polymer. Prior to the application of the second solution to the web, any excess of the first solution may be removed, e.g., by mechanical wiping using a wiper blade or the like, padding, etcetera. Preferably, prior to the application of the second solution to the web, a sufficient portion of the first solution is removed so that the web is not fully wetted, i.e., saturated, with the first solution when the second solution is applied.

After the second solution has been applied and the web preferably fully wetted with a mixture of the first and second solutions, it is necessary to work the wetted web to mix the first solution and second solution, thereby facilitating the precipitation of the binder resin or polymer and the distribution thereof as a coating on the surfaces of the microfibers making up the worked web. This working can be carried out by a variety of techniques, including mechanical agitation, the action of tensioned wiper blades or subjecting the web to pressure between two rollers or a roller and a flat surface.

The filter sheets of this type have positive zeta potentials over the pH range of from 3 to 10, and when used as the first filter medium in the subject invention typically have absolute pore ratings in the range of from about 0.5 to about 1.0 micrometer or higher. Typically they have rinse up times to produce ultrapure water of resistivity greater than 14 megaohms/cm of less than 10 minutes.

Preferred base web materials for preparing the hydrophilic, microfibrous, polymeric filter sheets of this type are hydrophobic, polymeric webs comprised of microfibers of polyolefins, polyesters or polyamides, including polypropylene, polyethylene, polybutylene terephthalate, polyethylene terephthalate, nylon 66, nylon 6, nylon 610 and nylon 11. Preferred binder resins or polymers for use in preparing these types of microfibrous, polymeric filter sheets are the epoxy-based, water-soluble resins, such as the epoxy-functional polyamido/polyamino-epichlorohydrin resins. Particularly preferred are the epoxy-functional polyamine/epichlorohydrins containing quaternary ammonium groups. Preferred precipitating agents may be selected from a group of synthetic, water-soluble or dispersible polymers containing carboxylate groups, such as acrylic acid resins.

FILTER MEDIUM WITH A NEGATIVE ZETA POTENTIAL

To perform satisfactorily as the filter medium with a negative zeta potential in the downstream position, i.e., as the second filter medium, the particular medium chosen should have the following characteristics:

(1) a negative zeta potential under the conditions encountered in the filtering operation;

(2) a microporous structure, typically with an absolute pore rating of from about 0.01 to about 0.1 micrometer, and in all cases finer than that of the upstream or first filter medium; and (3) be hydrophilic.

When a filter medium with a negative zeta potential is used as the upstream filter medium, it should have the same characteristics described in (1) to (3) above except that the absolute pore rating must be less fine than that of the downstream or second filter. Typically, then, the absolute pore rating will be increased to the range of from about 0.05 to about 1.0 micrometer, typically from about 0.1 to about 0.5 micrometer.

The skinless, hydrophilic, microporous, polyamide membranes of U.S. Pat. No. 4,340,479, entitled "Process For Preparing Hydrophilic Polyamide Membrane Filter Media And Product" describes a preferred class of filter media meeting the criteria set forth above.

Basically, the hydrophilic, microporous, polyamide filter membranes disclosed in U.S. Pat. No. 4,340,479, the disclosure of which is incorporated herein by reference, are membranes prepared from alcohol-insoluble polyamide resins having a methylene to amide ratio in the range of about 5:1 to about 7:1. Membranes of this group include copolymers of hexamethylene diamine and adipic acid (nylon 66), copolymers of hexamethylene diamine and sebacic acid (nylon 610), homopolymers of poly-e-caprolactam (nylon 6) and copolymers of hexamethylene diamine and azelaic acid (nylon 69). Nylon 66 is preferred. Hydrophilic, microporous, polyamide membranes (nylon 66) of this type having absolute pore ratings from about 0.02 to 8 micrometer or greater are available from Pall Corporation under the trademark Ultipor ® $N_{66}$. These untreated membranes have negative zeta potentials in alkaline media, that is from about pH 6.5 and up.

In the process for manufacturing the membranes of U.S. Pat. No. 4,340,479, the polyamide resin is dissolved in a solvent system, such as a mixture of formic acid and water, and a nonsolvent, such as water, is added under controlled conditions of agitation to achieve nucleation of the solution.

In inducing nucleation of the polyamide solution, a visible precipitate is formed. This precipitate may partially or completely redissolve. Preferably, any visible particles which do not redissolve should be filtered out of the system, e.g., with a 10 micrometer filter, prior to casting the nucleated solution or casting composition.

The nucleated solution or casting composition is then cast onto a substrate, e.g., a porous polyester sheet or web or a non-porous polyester sheet, in the form of a film and this film of solution is then contacted with and diluted by a liquid nonsolvent system which is a mixture of a solvent and a nonsolvent for the polyamide resin. A preferred nonsolvent liquid system for preparing the polyamide membranes of U.S. Pat. No. 4,340,479 is a solution of water and formic acid, with the formic acid preferably present in the solution in an amount of from about 35 percent to about 60 percent by weight. The polyamide resin thereupon precipitates from the solution forming a hydrophilic membrane sheet on the substrate which can be washed to remove the solvent. The membrane can then be stripped from the substrate and dried or, if the substrate is porous, it can be incorporated in the membrane to serve as a permanent support, in which event it is dried with the membrane. If the substrate is to be incorporated into the membrane, it should be porous and capable of being wetted and impregnated by the casting composition, e.g., a porous, fibrous, polyester sheet with an open structure. By appropriate control of process variables, membranes with through pores of uniform size and shape can be obtained. Conversely, if desired, tapered through pores, wider at one surface of the sheet and narrowing as they proceed toward the opposite surface of the sheet, can be obtained.

When the filter medium with a negative zeta potential is used as the first filter medium or the upstream prefilter, the hydrophilic, polyamide membranes of U.S. Pat. No. 4,340,479 are still preferred. However, membrane material with absolute pore ratings typically in the range of from about 0.05 to 1.0 micrometer, preferably from about 0.05 to about 0.2 micrometer, are preferably used to reduce the tendency for the first filter medium to clog.

The hydrophilic polyamide membranes of U.S. Pat. No. 4,340,479 have a negative zeta potential at about pH 6.5 and above, making them useful as the negative zeta potential filter medium under most normally encountered operating conditions.

A class of surface controlled microporous, hydrophilic polyamide membranes which maintains their negative zeta potential over the broad pH range of from 3 to 10 are those of the type disclosed in U.S. Ser. No. 346,118, filed Feb. 5, 1982, the disclosure of which is incorporated herein by reference. Their method of preparation is as follows:

COCASTING TECHNIQUE OF U.S. SER. NO. 346,118

Surface modified, hydrophilic, microporous polyamide membranes with negative zeta potentials over the pH range of from 3 to 10 are prepared by the steps of (1) preparing a casting solution comprised of (A) a casting resin system comprised of (a) an alcohol-insoluble polyamide resin having a ratio $CH_2$:NHCO of methylene $CH_2$ to amide NHCO groups within the range from about 5:1 to about 7:1, nylon 66 being a preferred polyamide resin, and (b) a water-soluble, membrane surface modifying polymer having functional polar groups, such as carboxyl and sulfonic, and a molecular weight of 10,000 or greater; and (B) a solvent system (such as formic acid and water) in which the casting resin system is soluble; (2) inducing nucleation of the casting solution by controlled addition of a nonsolvent (such as water) for the casting resin system under controlled conditions of concentration, temperature, addition rate and degree of agitation to obtain a visible precipitate of casting resin system particles which may or may not thereafter partially or completely redissolve, thereby forming a casting composition; (3) preferably filtering the casting composition to remove visible precipitated particles; (4) spreading the casting composition on a substrate to form a thin film thereof on the substrate; (5) contacting and diluting the film of casting composition with a liquid nonsolvent system comprised of a mixture of solvent (formic acid) and nonsolvent (water) liquids and containing a substantial porportion of the solvent liquid (formic acid) but less than the proportion in the casting composition, thereby precipitating the casting resin system from the casting composition in the form of a thin, skinless, hydrophilic, surface modified, microporous membrane; (6) washing the membrane to remove solvent; and (7) drying the membrane.

The resulting surface modified, alcohol-insoluble polyamide membranes are hydrophilic, have absolute pore ratings of from about 0.01 to about 10 micrometers or more, and have negative zeta potentials over the pH range of from 3 to 10.

The membrane surface modifying polymers or resins useful in preparing membranes of this type are water-soluble polymers with molecular weights of 10,000 or greater, preferably 20,000 or greater, such as carboxyl-containing polymers, such as polymers of acrylic acid, and sulfonic-containing compositions, such as a homopolymer of styrene sulfonic acid.

When negative zeta potential membranes of this type are used as the second filter medium in the downstream position, they will typically have absolute pore ratings of from about 0.01 to about 0.1 micrometer, preferably from about 0.02 to about 0.06 micrometer. When used as the first filter medium in the upstream position, they will typically have absolute pore ratings of from about 0.05 to about 1.0 micrometer, preferably from about 0.05 to about 0.2 micrometer.

FORMS OF THE FILTER SYSTEM

The filter systems of the subject invention operate in a series mode. That is, the fluid medium contaminated with submicronic particulate matter is passed through the first filter medium (the prefilter which removes larger particles by a sieve mechanism as well as either electronegatively or electropositively charged particles by adsorption). The fluid from the first filter medium (which is now substantially free of fine particulate matter having a charge opposite to the zeta potential of the first filter medium) is then passed through the second filter medium (also referred to as the final filter) which removes the remaining electrically charged particles of opposite sign from those removed on the first filter and, by a sieve mechanism, removes uncharged or neutral particulates. The second filter medium operates as a last chance or final filter removing any particulate matter larger than the absolute pore rating of the final filter.

The form that the serially operating filter system takes may vary. For example, a composite filter sheet comprised of a first and second filter medium may be formed and used as a flat, planar sheet. Alternatively, the composite sheet may be formed into a pleated or accordion form and used in a conventional element such as a cartridge. As another alternative, the first and second filter media can be formed as separate sheets which can independently be formed into elements and incorporated into separate cartridges of the type conventional in the industry and then used in a series arrangement.

As will be evident from the following examples, the filter system of the subject invention provides an economical means for enhanced removal of fine particulate contaminants from fluid media, particularly particulates in the ultrafine region, at essentially absolute efficiencies, i e., 99.99 percent or higher, and in many instances at substantially higher levels. Additionally, the subject invention provides a novel and economic way for processing ultrapure water approaching theoretical resistivity, i.e., free from contamination from dissolved or suspended material, such as for use in electronics manufacture and other applications requiring pure water free from particulates and ionic impurities. It should also be recognized that the filter system of this invention can be used downstream of a coarse prefilter which removes relatively coarse particulate matter, e.g., on the order of 1 to 30 micrometers or greater. By removing coarse or gross particulate matter prior to contacting the contaminated fluid with the filter system of this invention, the life of the subject filter system will be extended.

METHOD OF TESTING THE FILTER SYSTEM OF THE FOLLOWING EXAMPLES

The properties of the filter systems of the following examples were evaluated by a variety of test methods as described below:

(a) Zeta Potential

Zeta potentials are calculated from measurements of the streaming potentials generated by flow of a 0.001 weight percent solution of KCl in distilled water through several layers of the filter membrane secured in a filter sheet holder. Zeta potential is a measure of the net immobile electrostatic charge on a membrane surface exposed to a fluid. It is related to the streaming potential generated when that fluid flows through the filter sheet by the following formula (J. T. Davis et al, *Interfacial Phenomena*, Academic Press, New York, 1963):

$$\text{Zeta Potential (mV)} = \frac{4\pi\eta}{D} \cdot \frac{E_s \lambda}{P}$$

wherein $\eta$ is the viscosity of the flowing solution, D is the dielectric constant of the solution, $\lambda$ is its conductivity, $E_s$ is the streaming potential, and P is the pressure drop across the filter sheet during the period of flow. In the following examples, the quantity $4\pi\eta/D$ is constant, having the value $2.052 \times 10^{-2}$, making the zeta potential equal to:

$$\text{Zeta Potential (mV)} = \frac{2.052 \times 10^{-2} \cdot E_s \text{ (Volt)} \cdot \lambda \text{ (umho/cm)}}{P}$$

(b) Latex Particle Removal

Monodisperse suspensions of polystyrene latex with well-characterized particle sizes (available from Dow Diagnostics Inc.) were prepared in approximate 0.1 percent by weight solutions in deionized water containing 0.1 percent Triton X-100 (an adduct of nonyl phenol with about 10 moles of ethylene oxide). Latex suspensions were pumped through the filter systems positioned in a disc holder 47 millimeters in diameter and having an effective filtration area of 0.01 square feet (9.29 cm$^2$) using a Sage Instrument Model 341 syringe pump at a rate of 2 milliliters per minute. The effluent was passed through an optical flow cell in a light scattering photometer (Model 2000D, available from Phoenix Precision Instrument Inc.). The scattering signal from a beam of 537 nm light, measured at 90 degrees, was converted to latex bead concentration by means of an empirically determined concentration-scattering intensity correlation for each latex size. Latex bead capacities were derived from measured efficiencies and total volume of latex bead challenge by the following formula:

$$\frac{\text{concentration of input (0.1\%)}}{\text{concentration of effluent}} = \beta$$

$$\% \text{ removal efficiency} = \frac{\beta - 1}{\beta} \times 100.$$

(c) Resistivity Test

The effluent water from the filter systems of the examples was monitored for resistivity with a Model 3418 conductivity cell (Yellow Springs Instrument Company). The conductivity cell was connected to a Model 31 conductivity bridge (Yellow Springs Instrument Company) which allowed the direct measurement of effluent resistivity.

EXAMPLE 1

(A) A skinless, surface modified, hydrophilic, microporous polyamide (nylon 66) membrane with a positive zeta potential under the conditions encountered in this example and an absolute pore rating of about 0.1 micrometer was converted to a pleated filter cartridge with a membrane area of about 9 square feet (cartridge 1).

In like manner, a skinless, hydrophilic, microporous polyamide (nylon 66) membrane with a negative zeta potential under the conditions encountered in this example and an absolute pore rating of about 0.04 micrometer was converted to a pleated filter cartridge with a membrane area of about 9 square feet (cartridge 2).

Industrial plant water, containing native pseudomonas-type bacteria in concentrations varying from 100 organisms per liter to greater than 1000 organisms per liter, was passed serially through cartridge 1 and then through cartridge 2 at a constant flow rate of about 2 gallons per minute.

The filtrate water delivered by this filter system was periodically monitored for the presence of bacteria by standard microbiological procedures and found to be bacterially sterile for a period of 53 days, after which time the test was discontinued. These results indicate that the filter system of Example 1(A) functions as an absolute bacterial filter to provide a bacteria free (sterile) filtrate water.

(B) A skinless, surface modified, hydrophilic, microporous polyamide (nylon 66) membrane with a positive zeta potential under the conditions encountered in this example and an absolute pore rating of about 0.1 micrometer (membrane A) and a skinless, hydrophilic, microporous polyamide (nylon 66) membrane with a negative zeta potential under the conditions encountered in this example and an absolute pore rating of about 0.04 micrometer (membrane B) were assembled into a composite layered membrane system and secured in a conventional membrane holder with membrane A mounted upstream of membrane B The membrane system was then challenged with an aqueous suspension of latex spheres with a mean diameter of 0.038 micrometer. A latex removal efficiency greater than 99.99 percent was measured at a total latex sphere challenge level of 0.1 gram per square foot membrane surface.

(C) A skinless, surface modified, hydrophilic, microporous polyamide membrane with a positive zeta potential under the conditions encountered in this example and an absolute pore rating of about 0.1 micrometer was converted into a filter element with a membrane area of about 9 square feet (element A). In like manner, a skinless, hydrophilic, microporous polyamide membrane with a negative zeta potential under the conditions encountered in this example and an absolute pore rating of about 0.04 micrometer was converted into a second element with a membrane area of about 9 square feet (element B). The same polyamide membrane was used to prepare the filter cartridge 1 of (A) above, the membrane A of (B) above and element A of (C). Similarly, the same polyamide membrane was used to prepare the filter cartridge 2 of (A) above, the membrane B of (B) above and element B of (C).

The two elements were then employed as a filter system operating in series with element A preceding or upstream of element B. Electronics grade water of resistivity greater than 14 megaohms/cm was flowed through the filter system at a flow rate of about 2 gallons per minute. After 7 minutes of onstream time, the resistivity of the effluent was measured to be greater than 14 megaohms per centimeter, as required for electonics process application.

(D) A skinless, surface modified, hydrophilic, microporous polyamide (nylon 66) membrane with a positive zeta potential under the conditions encountered in this example and an absolute pore rating of about 0.1 micrometer (membrane A) and a skinless, hydrophilic, microporous polyamide (nylon 66) membrane with a negative zeta potential under the conditions encountered in this example and an absolute pore rating of about 0.04 micrometer (membrane B) were assembled into a composite layered membrane system and secured in a conventional membrane holder with membrane A mounted upstream of membrane B. The membrane system was then challenged with an aqueous suspension of mycoplasma (acholeplasma laidlawii, ATCC 2320 to a total challenge level of $1.8 \times 10^{11}$ organisms per square foot membrane area. Analysis of the effluent from the filter system by standard microbiological procedures demonstrated that the effluent was free from mycoplasma and hence the filter system operated with a removal efficiency in excess of 99.9999999994 percent.

It is not uncommon for water supplies to contain $10^4$ to $10^6$ bacteria per liter, and for a filter cartridge rated at 10 liters/minute to be on stream for 10,000 hours. Thus, such a filter may have incident on it as many as $6 \times 10^{11}$ bacteria during its lifetime. The efficiency of such a filter must therefore be in excess of $$\left(1 - \frac{1}{6 \times 10^{11}}\right) \times 100 = 99.9999999998\%$$

In order to avoid the use of so many numerals, this same requirement can be concisely expressed by stating that the titre reduction ($T_R$) which is the ratio of influent to effluent concentration must exceed $6 \times 10^{11}$, and efficiency for any given $T_R$ can be calculated from $$\text{Efficiency, \%,} = \left(1 - \frac{1}{T_R}\right) \times 100$$

Conventional ultrafilters operate typically in the $T_R$ range of $10^3$ to $10^7$, and thus a 10 liter per minute ultrafilter could pass 10,000 or more bacteria during a 10,000 hour service period.

The results as set out in the above example establish the filter systems of the subject invention are capable of (1) sterilizing filtrate water by complete removal of incident bacteria, i.e., 100 percent efficiency at high capacities, (2) capable of efficiently removing very fine particulate material at high efficiencies (99.99 percent) and at high loadings (0.1 gram per square foot) and (3) capable of delivering water of near theoretical resistivity, i.e., greater than 14 megaohms/cm resistivity, after short onstream time. This filter system, then, provides high purity water free from bacterial contamination, particulate and ionic contaminants and therefore is particularly desirable for electronic filtration applications.

When these capabilities are combined with high flow rates at relatively low pressure drops, e.g., 20 psi or less, vis-a-vis conventional skinned membranes operating at pressures in the neighborhood of 40 psi coupled with the inability to provide bacterially sterile filtrates and having limited loading capacities, the desirablity of the subject invention is manifest.

EXAMPLE 2

A first filter system comprised of a composite of (1) a first or upstream skinless, hydrophilic, microporous, nylon 66 membrane having a negative zeta potential under the conditions encountered in this example and an absolute pore rating of about 0.1 micrometer and (2) a second or downstream skinless, hydrophilic, microporous nylon 66 membrane also having a negative zeta potential under the conditions encountered in this example but an absolute pore rating of about 0.04 micrometer was prepared (filter system I).

In like manner, a second filter system was prepared of first and second hydrophilic, microporous nylon 66 membranes having the same respective pore ratings as described for the first and second membranes of filter system I above but with the first or upstream hydrophilic nylon 66 membrane being surface modified and having a positive zeta potential (filter system II).

Filter system I and filter system II were each challenged independently with a solution of 0.038 micrometer latex beads in a water suspension (concentration of the latex beads in the water was 0.01 weight percent). The capacity of the two filter systems for 0.038 micrometer latex while operating at an efficiency of 99.995 percent was determined with the results set out below:

(1) filter system I had a capacity of 0.03 grams per square foot of filter surface when challenged at a rate of 200 milliliters of the dispersion per square foot per minute;

(2) filter system II had a capacity of 0.11 grams per square foot when challenged with the latex bead suspension at a rate of 200 milliliters per square foot of filter surface per minute.

These results show a nearly four-fold increase in capacity when operating at this high efficiency for the filter system of the subject invention combining a positive zeta potential first filter with a downstream finer pored negative zeta potential filter when compared with filter system I.

EXAMPLE 3

Two cartridge elements having pleated filter membranes, each with about 9 square feet of filter surface area and with the characteristics set out below, were mounted in series relationship. The first element contained a surface modified, hydrophilic, microporous nylon 66 membrane having a positive zeta potential and an absolute pore rating of 0.1 micrometer. The second element contained a hydrophilic, microporous, nylon 66 membrane having a negative zeta potential and an absolute pore rating of 0.04 micrometer.

An influent stream of ultrapure water with a resistivity of 18 megaohms per centimeter was filtered through the two element filter system described above, flowing in series through the first element and then through the second element, at a constant flow rate of 2 gallons per minute.

Within 15 minutes the effluent water from the two stage filter system had a resistivity of about 18 megaohms per centimeter indicating that the filter was quickly purged of any contaminants and was then capable of operation at a high purity level. After about 30 minutes of onstream time, the influent water to the two stage filter system was contaminated with a low level of tap water, reducing the influent water purity and lowering its resistivity to a constant level of about 12 megaohms per centimeter. Under these conditions, the resistivity of the effluent water from the two stage filter system dropped for a brief period and then recovered in less than 1 minute to 14 megaohms per centimeter and within about 5 minutes had risen to about 18 megaohms per centimeter, all while the influent water resistivity remained at 12 megaohms. The system was run for about an additional 5 minutes before being shut down and, over that time span, the resistivity of the effluent water remained at 14 megaohms per centimeter or better.

This example demonstrates that a filter system of this invention when operating as a last chance or final filter has the ability to control upsets in the purity of water prepared in an ultrapure water filtration system, upsets which can occur frequently due to the very low level of impurities necessary to cause an upset. This ability is particularly important in systems conventionally used to prepare deionized water where a mixed ionic bed of ion exchange particles is used to insure the removal of both positive and negative contaminants. In such a case, the particulate matter needed to be removed in a last chance or final filter may be either positive or negative. The subject filter system removes both positive and negative particles in a very efficient manner when such an upset occurs.

Other tests of filter systems of the subject invention have demonstrated the ability to remove from aqueous solutions (1) dextrans in the molecular weight range of from $2 \times 10^6$ to $5 \times 10^6$ Daltons, (2) an uncharged endotoxin molecule of molecular weight of about 30,000 Daltons with efficiencies greater than 99.998 percent and (3) 0.021 micrometer silica particles and 0.038 micrometer latex beads at efficiencies greater than 99.99 percent.

When filter systems of this invention are used to treat water for use in microelectronics manufacture and the like where a resistivity of greater than 14 megaohms/cm is required, the surface modified filter media used in preparing the filter systems of this invention are flushed with an aqueous ammonium hydroxide solutions, e.g., a 0.2 molar solution, to convert quaternary ammonium groups to the hydroxide form. This can be carried out in any convenient manner; for example, after formation into element form as was done in Examples 1 (C) and 3.

INDUSTRIAL APPLICABILITY

The essentially absolute efficiency of the filter system of this invention in removing ultrafine particulates, including both electropositively and electronegatively charged particles, the ability to remove bacteria at an absolute level providing a bacterially free, sterile effluent, and the ability to provide ultrapure water of near theoretical resistivity after short onstream times, and the ability to deliver water with increased resistivity and hence greater purity compared with the influent water, have been demonstrated. Because of these characteristics of the filter systems of this invention and coupled with their ability to be both manufactured and operated in an economical manner, the filter systems of this invention find use in industry and the medical field to treat water supplies for critical application such as water for injection into humans, in microelectronics manufacture, in filtration of blood serum to help achieve sterility, for filtration of parenterals, and generally for any use where an ionizing liquid is to be filtered to a high degree of clarity and purity.

It will be apparent that different embodiments of this invention may be made without departing from the spirit and scope thereof, and therefore it is not intended to be limited except as indicated in the appended claims.

What is claimed is:

1. A process for the filtration of a contaminated fluid comprising ultrafine particulate material with particle sizes in the range of from about 0.001 to about 10 micrometers said process comprising:
   (a) passing said fluid through a first filter medium comprised of a surface modified, hydrophilic, microporous member, said first filter medium further characterized by (i) an absolute pore rating in the range of from about 0.05 to about 1.0 micrometer and (ii) a positive zeta potential, to remove electronegatively charged particulate matter from said fluid; and
   (b) then passing said fluid through a second filter medium comprised of a hydrophilic, microporous member, said second filter medium further characterized by (1) an absolute pore rating finer than that of said first filter membrane and in the range of from about 0.01 to about 0.1 micrometer and (ii) a negative zeta potential, to form a filtrate substantially free of (1) both electronegatively and electropositively charged particulate matter, (2) bacteria and endotoxins, and (3) particulate matter greater in size than the absolute pore rating of said second filter medium.

2. The process of claim 1 wherein both said first filter medium and said second filter medium are comprised of nylon 66.

3. The process of claim 2 wherein said second filter medium has an absolute pore rating of from about 0.02 to about 0.06 micrometer.

4. The process of claim 2 wherein said contaminated fluid is water.

5. The process of claim 2 wherein said filtrate is comprised of ultrapure water having an effluent resistivity greater than 14 megaohms/cm.

6. A process for the filtration of a contaminated fluid comprising ultrafine particulate matter with particle sizes in the range of from about 0.001 to about 10 micrometers, said process comprising:
   (a) passing said fluid through a first filter medium comprised of a hydrophilic, microporous member said first filter medium further characterized by (i) an absolute pore rating in the range of from about 0.05 to about 1.0 micrometer and (ii) a negative zeta potential, to remove electropositively charged particulate matter from said fluid; and
   (b) then passing said fluid through a second filter medium comprised of a surface modified, hydrophilic, microporous member said second filter medium further characterized by (i) an absolute pore rating finer than that of said first filter membrane and in the range of from about 0.01 to about 0.1 micrometer and (ii) a positive zeta potential, to form a filtrate substantially free of (1) both electronegatively and electropositively charged particulate matter, (2) bacteria and endotoxins, and (3) particulate matter greater in size than the absolute pore rating of said second filter medium.

7. The process of claim 6 wherein both said first filter medium and said second filter medium are comprised of nylon 66.

8. The process of claim 7 wherein said second filter medium has an absolute pore rating of from about 0.02 to about 0.06 micrometer.

9. The process of claim 7 wherein said contaminated fluid is water.

10. The process of claim 7 wherein said second filtrate is comprised of ultrapure water having an effluent resistivity greater than 14 megaohms/cm.

11. A filter system comprising, in combination, a first filter medium comprised of a surface modified, hydrophilic, microporous member having a positive zeta potential and an absolute pore rating in the range of from about 0.05 to about 1.0 micrometer and a second filter medium comprised of a hydrophilic, microporous member having a negative zeta potential and an absolute pore rating in the range of from about 0.01 to about 0.1 micrometer and finer than that of said first filter medium.

12. The filter system of claim 11 wherein both said first filter medium and said second filter medium are comprised of nylon 66.

13. The filter system of claim 12 wherein said filter system is formed into a filter element.

14. The filter system of claim 12 wherein said filter system comprises a pleated filter element in cartridge form.

15. The filter system of claim 12 wherein said system is capable of providing a filtrate of ultrapure water having a resistivity greater than 14 megaohms/cm. after a rinse up time of less than 10 minutes.

16. A filter system comprising, in combination, a first filter medium comprised of a hydrophilic, microporous polyamide membrane having a negative zeta potential and an absolute pore rating in the range of from about 0.05 to about 1.0 micrometer and a second filter medium comprised of a surface modified, hydrophilic, microporous polyamide membrane having a positive zeta potential and an absolute pore rating in the range of from about 0.01 to about 0.1 micrometer and finer than that of said first filter medium.

17. The filter system of claim 16 wherein said first filter medium and said second filter medium are comprised of nylon 66.

18. A filter system comprising, in combination, a first filter medium comprised of a surface modified, hydrophilic, microporous polyamide membrane containing quaternary ammonium groups in the hydroxide form and having a positive zeta potential and an absolute pore rating of from about 0.05 to about 1.0 micrometer and a second filter medium comprised of a hydrophilic, microporous polyamide membrane having a negative zeta potential and an absolute pore rating in the range of from about 0.01 to about 0.1 micrometer and finer than that of said first filter medium.

19. The filter system of claim 18 wherein said first filter medium has been contacted with an aqueous solution of ammonium hydroxide to convert said quaternary ammonium group to the hydroxide form.

* * * * *